United States Patent
Sickler (10) Patent No.: US 10,195,096 B1
(45) Date of Patent: Feb. 5, 2019

(54) FEMININE HYGIENE PRODUCT DISPENSER

(71) Applicant: Juli Sickler, Bismarck, ND (US)

(72) Inventor: Juli Sickler, Bismarck, ND (US)

(*) Notice: Subject to any disclaimer, the term of this patent is extended or adjusted under 35 U.S.C. 154(b) by 0 days.

(21) Appl. No.: 15/811,813

(22) Filed: Nov. 14, 2017

(51) Int. Cl.
*A61F 15/00* (2006.01)
*A45D 40/22* (2006.01)
*A45D 40/24* (2006.01)

(52) U.S. Cl.
CPC .......... *A61F 15/003* (2013.01); *A45D 40/22* (2013.01); *A45D 40/24* (2013.01)

(58) Field of Classification Search
CPC ........ A61F 15/003; A45D 40/22; A45D 40/24
USPC .......... 62/457.4, 3.64; 211/59.2, 92; 221/92, 221/301, 289, 299, 290, 194, 150 R, 283, 221/285, 261
See application file for complete search history.

(56) References Cited

U.S. PATENT DOCUMENTS

| | | | | |
|---|---|---|---|---|
| 2,711,241 A * | 6/1955 | Abrahamsen | ............ | F25D 25/00 193/27 |
| 4,132,214 A * | 1/1979 | Schnurr | ............... | A63B 47/002 124/1 |
| 4,235,351 A * | 11/1980 | Kolbl | ............ | G07F 11/30 221/301 |
| 4,308,974 A * | 1/1982 | Jones | ............ | A61F 15/001 221/196 |
| 4,405,059 A * | 9/1983 | Kull | ............ | B65G 1/08 221/129 |
| 4,676,074 A * | 6/1987 | Morgan, Jr. | ............ | G07F 11/30 221/150 R |
| 4,729,480 A * | 3/1988 | Groover | ................ | G07F 11/28 211/59.2 |
| 4,750,640 A | 6/1988 | Kobeck | | |
| D380,114 S | 6/1997 | Albright | | |
| 6,173,582 B1 * | 1/2001 | Hixson | ................ | A47F 1/087 62/3.64 |
| 6,206,237 B1 * | 3/2001 | Dillon | ............ | B65G 1/08 221/193 |
| 6,862,896 B1 * | 3/2005 | Seidl | ............ | F25D 3/08 220/592.16 |
| 8,261,940 B2 * | 9/2012 | Pfister | ............ | G07F 11/04 221/123 |
| 9,572,730 B2 * | 2/2017 | Young | ............ | A61F 13/5515 |

(Continued)

FOREIGN PATENT DOCUMENTS

WO 2009094789 8/2009

Primary Examiner — Rakesh Kumar (57) ABSTRACT

The feminine hygiene product dispenser comprises an enclosure having a pivoting compartment and a drawer. Interior space of the enclosure is filled with individually wrapped feminine hygiene products such as tampons. The pivoting compartment comprises a concave trough into which a feminine hygiene product may drop when the pivoting compartment is in a closed position. The pivoting compartment may be moved to an open position by pressing down on a lip that extends across the pivoting compartment. When the pivoting compartment is moved to the open position, the feminine hygiene product is passed to the exterior of the enclosure and may be taken by a user. The pivoting compartment is spring loaded and, when released, returns to the closed position where another of the products may drop into the concave trough. The drawer may be used to hold other feminine hygiene products such as pads and panty liners.

5 Claims, 5 Drawing Sheets

(56) References Cited

U.S. PATENT DOCUMENTS

| | | |
|---|---|---|
| 2008/0169411 A1 | 7/2008 | Quinn |
| 2010/0051496 A1 | 3/2010 | Watson |
| 2011/0006074 A1* | 1/2011 | Machers ................. G07F 11/20 221/150 R |
| 2011/0024414 A1* | 2/2011 | Widmer ................... A47K 5/12 220/4.28 |
| 2014/0326722 A1 | 11/2014 | Dunbar |
| 2016/0175173 A1 | 6/2016 | Higgs-Jackson |

* cited by examiner

FIG. 4

FEMININE HYGIENE PRODUCT DISPENSER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of product dispensers, more specifically, a feminine hygiene produce dispenser.

SUMMARY OF INVENTION

The feminine hygiene product dispenser comprises an enclosure having a pivoting compartment and a drawer. Interior space of the enclosure is filled with individually wrapped feminine hygiene products such as tampons. The pivoting compartment comprises a concave trough into which a feminine hygiene product may drop when the pivoting compartment is in a closed position. The pivoting compartment may be moved to an open position by pressing down on a lip that extends across the pivoting compartment. When the pivoting compartment is moved to the open position, the feminine hygiene product is passed to the exterior of the enclosure and may be taken by a user. The pivoting compartment is spring loaded and, when released, returns to the closed position where another of the products may drop into the concave trough. The drawer may be used to hold other feminine hygiene products such as pads and panty liners.

An object of the invention is to dispense feminine hygiene products such as individually wrapped tampons, pads, and panty liners.

Another object of the invention is to dispense individually wrapped tampons via a pivoting compartment.

A further object of the invention is to provide a pivoting compartment that automatically returns to the closed position after each dispensing operation.

Yet another object of the invention is to provide a drawer for pads and/or panty liners using otherwise dead space in the enclosure.

These together with additional objects, features and advantages of the feminine hygiene product dispenser will be readily apparent to those of ordinary skill in the art upon reading the following detailed description of the presently preferred, but nonetheless illustrative, embodiments when taken in conjunction with the accompanying drawings.

In this respect, before explaining the current embodiments of the feminine hygiene product dispenser in detail, it is to be understood that the feminine hygiene product dispenser is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the feminine hygiene product dispenser.

It is therefore important that the claims be regarded as including such equivalent construction insofar as they do not depart from the spirit and scope of the feminine hygiene product dispenser. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
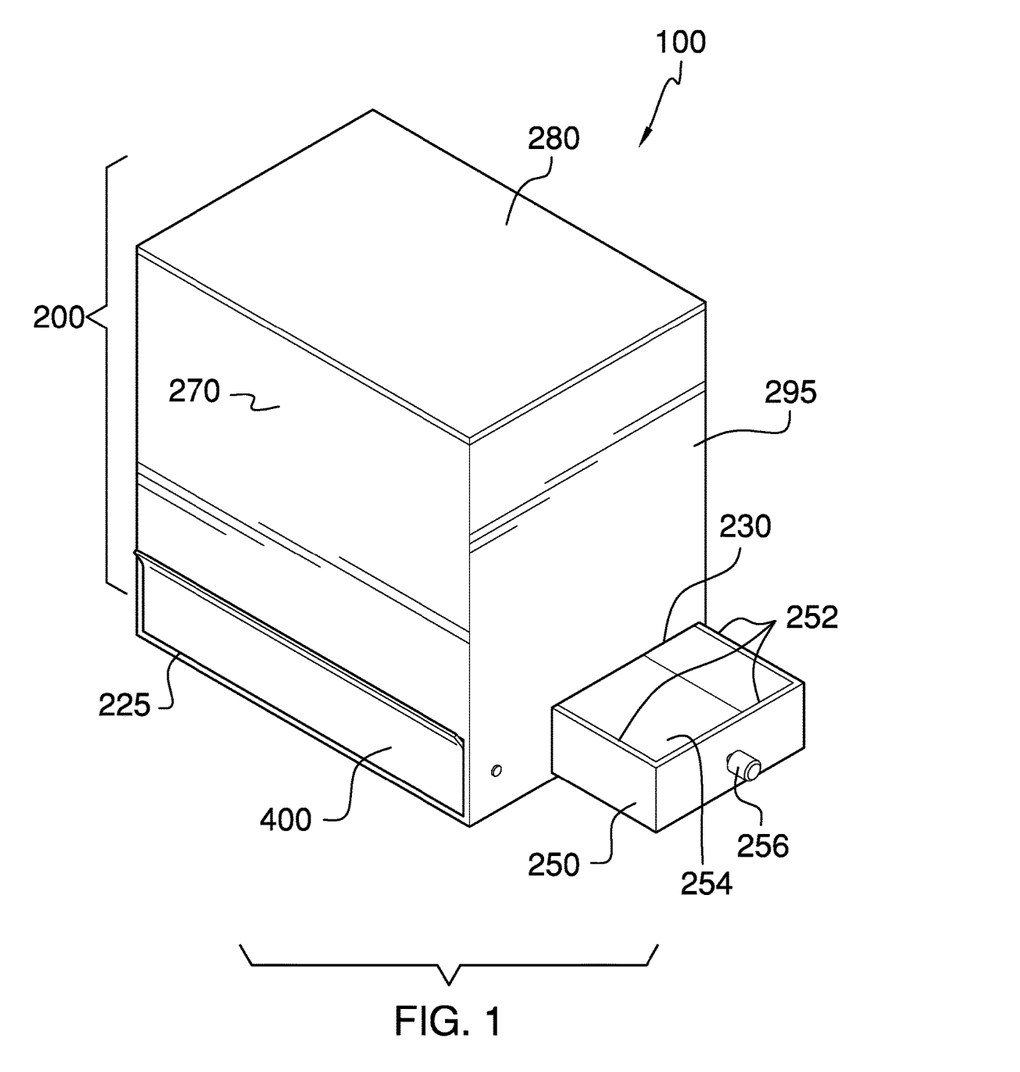
FIG. 1 is a perspective view of an embodiment of the disclosure.
Figure 2:
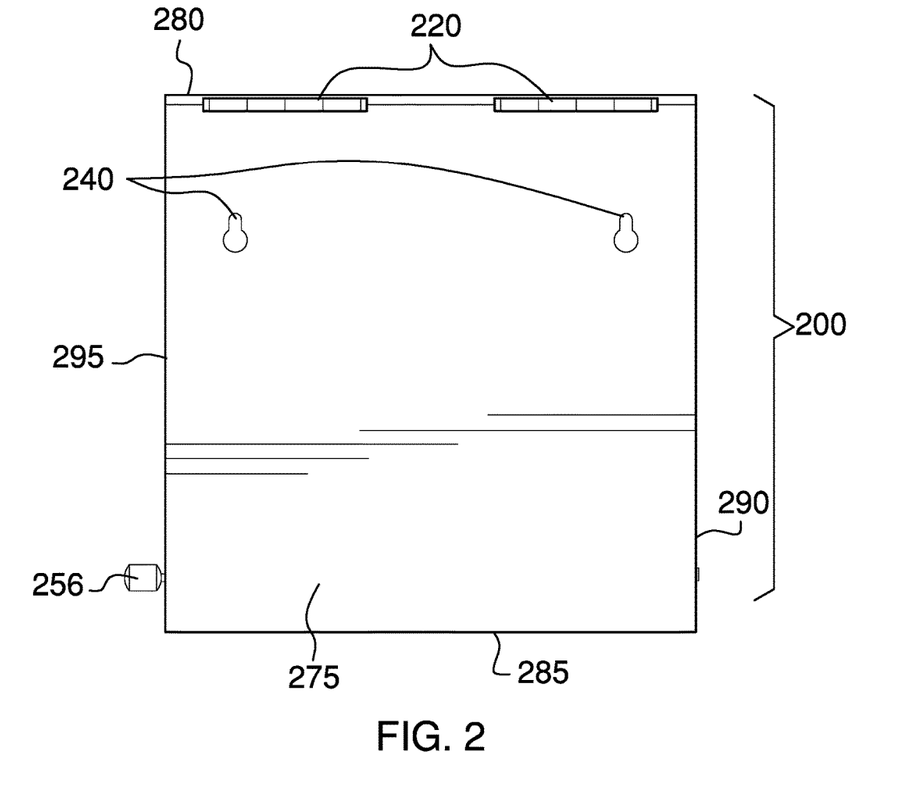
FIG. 2 is a rear view of an embodiment of the disclosure.
Figure 3:
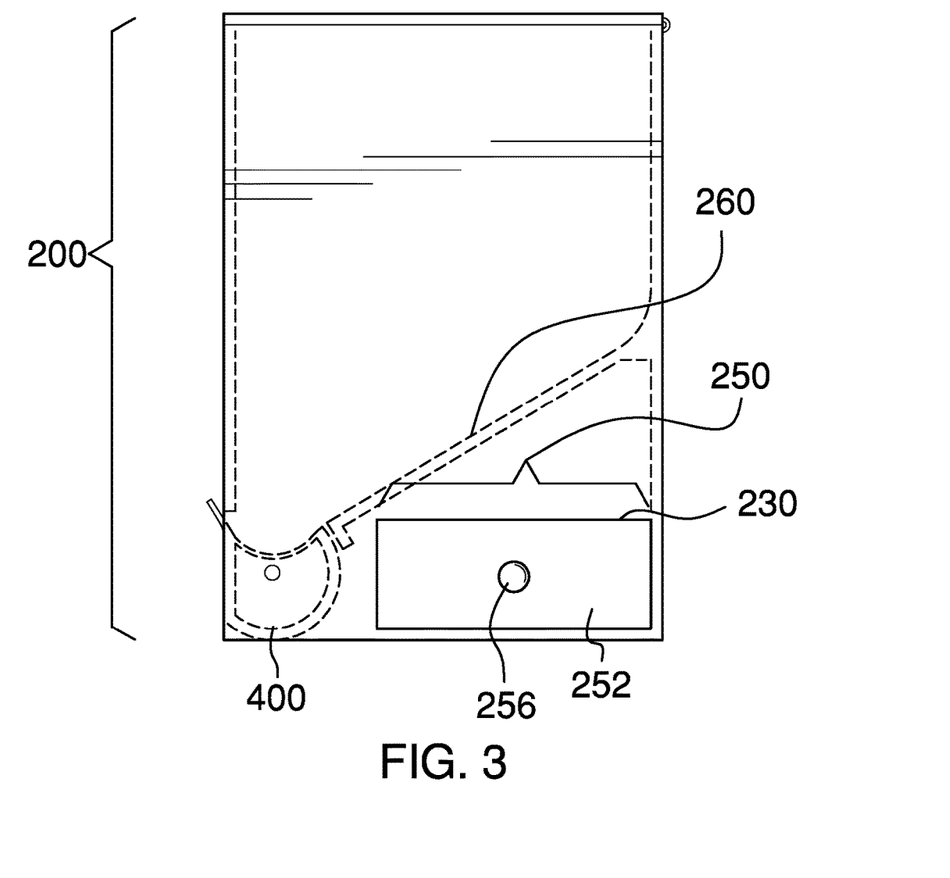
FIG. 3 is a side view of an embodiment of the disclosure.
Figure 4:
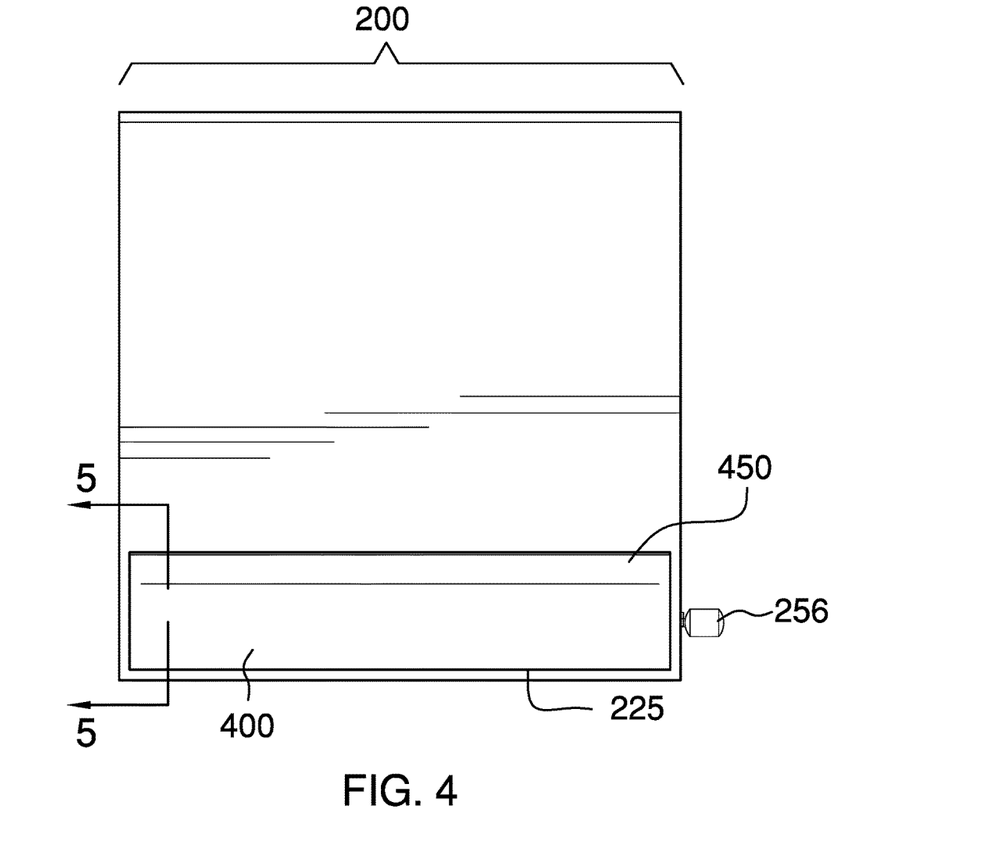
FIG. 4 is a front view of an embodiment of the disclosure.
Figure 5:
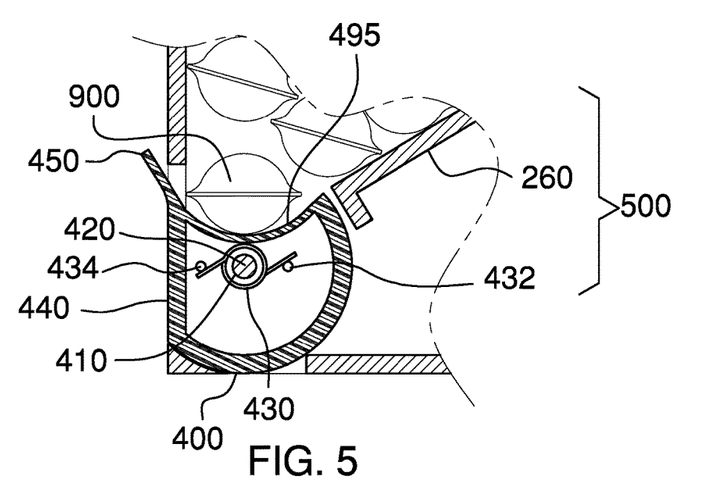
FIG. 5 is a cross-sectional view of an embodiment of the disclosure across 5-5 as shown in FIG. 4 showing the pivoting compartment in the closed position.
Figure 6:
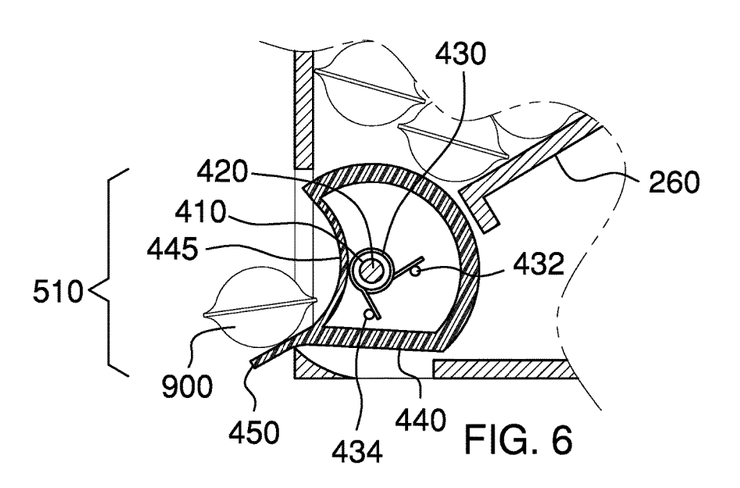
FIG. 6 is a cross-sectional view of an embodiment of the disclosure across 5-5 as shown in FIG. 4 showing the pivoting compartment in the open position.

Detailed reference will now be made to a first potential embodiment of the disclosure, which is illustrated in FIGS. 1 through 6.

The feminine hygiene product dispenser 100 (hereinafter invention) comprises an enclosure 200, a pivoting compartment 400, and a drawer 250. The invention 100 stores individually wrapped tampons 900 within the enclosure 200. The pivoting compartment 400 allows the individually wrapped tampons 900 to be removed one at a time. The drawer 250 may be used to hold other feminine products (not illustrated in the figures). As non-limiting examples, the other feminine products may comprise pads or panty liners.

The enclosure 200 stores the individually wrapped tampons 900 that are waiting to be dispensed. The enclosure 200 comprises a front wall 270, a rear wall 275, a top 280, a bottom 285, a left side wall 290, a right side wall 295, and an angled slide 260. The enclosure 200 may be wall-mounted using one or more mounting slots 240 or the enclosure 200 may be free-standing by resting the bottom 285 of the enclosure 200 on a table, counter, or other horizontal surface.

The angled slide 260 is located inside of the enclosure 200 and is oriented to be higher at the rear wall 275 and sloping down as it moves towards the front wall 270. The angled slide 260 is provided to force the individually wrapped tampons 900 towards the front of the enclosure 200 as they move down. As the individually wrapped tampons 900 are removed from the lower front of the enclosure 200, gravity pulls the individually wrapped tampons 900 that remain in the enclosure 200 down along the angled slide 260. The top 280 of the enclosure 200 is hinged using one or more hinges 220 thus forming a door that may be opened to replenish the supply of the individually wrapped tampons 900.

A first rectangular aperture 225 is provided at the bottom of the front wall 270 to allow the individually wrapped tampons to exit from the enclosure 200. The pivoting compartment 400 occupies the first rectangular aperture 225 and prevents the individually wrapped tampons 900 from falling out until one is needed. An axle 420 for the pivoting compartment 400 runs from the lower front corner of the left side wall 290 to the lower front corner of the right side wall 295.

A second rectangular aperture 230 is provided at the lower rear of the left side wall 290 or, in some embodiments, at the lower rear of the right side wall 295. The second rectangular aperture 230 is provided to allow the drawer 250 to slide out of the enclosure 200. The enclosure 200 may comprise additional drawer guide hardware (not illustrated in the figures) to guide the drawer 250 smoothly into and out of the enclosure 200.

The pivoting compartment 400 may be a container for the individually wrapped tampon 900 that is about to be dispensed. The pivoting compartment 400 is located at the bottom, front of the enclosure 200 where it fills the first rectangular aperture 225 in the front wall 270 of the enclosure 200. The pivoting compartment 400 comprises a hole 410 that runs longitudinally through the pivoting compartment 400. The axle 420 which is coupled to the left side wall 290 of the enclosure 200 and to the right side wall 295 of the enclosure 200 passes through the hole 410 and allows the pivoting compartment 400 to rotate.

The pivoting compartment 400 may be described as cylindrical with the following exceptions:

a flat face 440 may comprise the removal of material from the pivoting compartment 400 to form a plane surface where the pivoting compartment 400 would otherwise extend beyond the front wall 270 of the enclosure 200. When the pivoting compartment 400 is in a closed position 500, the flat face 440 aligns with the plane of the front wall 270 for appearance purposes.

a concave trough 445 may comprise the removal of material from the pivoting compartment 400 to form a curved and concave surface on the top of the pivoting compartment 400 when the pivoting compartment 400 is in the closed position 500. The concave trough 445 is provided to hold the individually wrapped tampon 900 that will be dispensed next. The concave trough 445 may run the entire length of the pivoting compartment 400. The concave trough 445 extends from the upper edge of the flat face 440 to the point where the angled slide 260 meets the pivoting compartment 400. The depth of the concave trough 445 is made deep enough to allow the individually wrapped tampon 900 to pass between the deepest part of the concave trough 445 and the upper edge of the first rectangular aperture 225 as the pivoting compartment 400 rotates from the closed position 500 to an open position 510.

a lip 450 comprises a projection along the length of the pivoting compartment 400. The lip 450 extends radially away from the center of the pivoting compartment 400 at the boundary between the flat face 440 and the concave trough 445. One purpose of the lip 450 is to stop rotation of the pivoting compartment 400 towards the closed position 500. Another purpose of the lip 450 is to provide an area where a user can grasp the pivoting compartment 400 and move the pivoting compartment 400 to the open position 510.

Although the previous description has described features of the pivoting compartment 400, such as the flat face 440 and the concave trough 445, in terms of the removal of material from the pivoting compartment 400, the features may in fact be molded into the pivoting compartment 400 when the pivoting compartment 400 is fabricated and may not require the removal of material to create the features.

The angled slide 260 and the concave trough 445 align in such a way that the individually wrapped tampons 900 may slide down the angled slide 260 and into the concave trough 445 without encountering an offset in height that might impede their movement.

The pivoting compartment 400 is spring-loaded, meaning that one or more springs 430 cause the pivoting compartment 400 to return to the closed position 500 after each use.

In some embodiments, the one or more springs 430 may be a coil of wire with straight ends that extend beyond the diameter of the coil. Looking for a moment at the right end of the pivoting compartment 400 (see FIG. 5 and FIG. 6), and recognizing that the invention 100 may comprise one of the one or more springs 430 at the left end of the pivoting compartment 400, at the right end of the pivoting compartment 400, or at both ends of the pivoting compartment 400, one of the straight ends of the coil may press against a first post 432 and the other one of the straight ends may press against a second post 434. The first post 432 may be permanently coupled to an interior surface of the right side wall 295 of the enclosure 200. The second post 434 may be permanently coupled to the end of the pivoting compartment 400. The placement and orientation of the first post 432, the second post 434, and rightmost of the one or more springs 430 may be such that the one or more springs cause the pivoting compartment 400 to rotate into the closed position 500 if the pivoting compartment 400 is left untouched. The force applied to the lip 450 to cause rotation of the pivoting compartment 400 into the open position 510 may increase tension on the one or more springs 430 such that when the lip is released the one or more springs 430 cause the pivoting compartment 400 to rotate back to the closed position 500. A similar description applies to the coil spring and posts located on the left side, if the embodiment provides them.

When the pivoting compartment 400 is in the closed position 500, the individually wrapped tampon 900 that is next to be dispensed drops into the concave trough 445 located at the top of the pivoting compartment 400. If the pivoting compartment 400 is rotated into the open position 510 the individually wrapped tampon 900 is moved out of the enclosure 200 and may be removed from the pivoting compartment 400. When the lip 450 is released, the pivoting compartment 400, now empty, returns to the closed position 500 where the concave trough 445 is refilled with another one of the individually wrapped tampons 900.

The drawer 250 may be provided to store feminine products and accessories. The drawer 250 comprises four side walls 252 plus a drawer bottom 254. One of the four side walls 252 may be exposed outside of the enclosure 200 and the exposed side wall may comprise a drawer pull 256. The drawer pull 256 may be accessible from outside of the enclosure 200 and may allow the drawer 250 to be pulled open.

The dimensions of the enclosure 200 are selected to accommodate the length of the individually wrapped tampons 900, to accommodate the size of pads and liners that may be placed in the drawer 250, and to provide sufficient capacity, in the form of internal volume of the enclosure 200, for the individually wrapped tampons 900 that are to be stored within the enclosure 200. In some embodiments, the enclosure 200 is 6 inches +/−2 inches wide as measured from the left side wall 290 to the right side wall 295, 6 inches +/−2 inches tall as measured from the top 280 to the bottom 285, and 4 inches +/−1 inch deep as measured from the front wall 270 to the rear wall 275.

As used herein, "align" means to place two or more components into positions and orientations which either arranges the components along a straight line or plane or which will allow the next step of assembly to proceed. As a non-limiting example, the next step of assembly may be to insert one component into another component.

As used in this disclosure, an "axle" is a cylindrical shaft that is inserted through the center of an object such that the center axis of the object and the center axis of the axle are aligned and the object can rotate using the axle as an axis of rotation.

As used in this disclosure, "concave" is used to describe a surface that resembles the interior surface of a sphere or a portion thereof.

As used herein, the words "couple", "couples", "coupled" or "coupling", mean connected, either directly or indirectly and does not necessarily imply a mechanical connection.

As used in this disclosure, a "diameter" of an object is a straight line segment that passes through the center (or center axis) of an object. The line segment of the diameter is terminated at the perimeter or boundary of the object through which the line segment of the diameter runs.

As used in this disclosure, a "drawer" is a storage compartment that is designed to slide into and out of a larger object.

As used in this disclosure, "horizontal" is a directional term that refers to a direction that is perpendicular to the local force of gravity. Unless specifically noted in this disclosure, the horizontal direction is always perpendicular to the vertical direction.

As used in this disclosure, the word "interior" is used as a relational term that implies that an object is located or contained within the boundary of a structure or a space.

As used in this disclosure, "orientation" refers to the positioning and/or angular alignment of a first object relative to a second object or relative to a fixed position, location, or direction.

As used in this disclosure, a "spring" is a device that is used to store mechanical energy. This mechanical energy will often be stored by deforming an elastomeric material that is used to make the device, by the application of a torque to a rigid structure, or by a combination thereof. In some embodiments, the rigid structure to which torque is applied may be composed of metal or plastic.

With respect to the above description, it is to be realized that the optimum dimensional relationship for the various components of the invention described above and in FIGS. 1 through 6, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A feminine hygiene product dispenser comprising:
an enclosure, a pivoting compartment, and a drawer;
wherein the feminine hygiene product dispenser stores individually wrapped tampons within the enclosure;
wherein the pivoting compartment allows the individually wrapped tampons to be removed one at a time;
wherein the drawer is used to hold other feminine products;
wherein the enclosure stores the individually wrapped tampons that are waiting to be dispensed;
wherein the enclosure comprises a front wall, a rear wall, a top, a bottom, a left side wall, a right side wall, and an angled slide;
wherein the angled slide is located inside of the enclosure and is oriented to be higher at the rear wall and sloping down as it moves towards the front wall;
wherein the angled slide is provided to force the individually wrapped tampons towards the front of the enclosure as they move down;
wherein the top of the enclosure is hinged using one or more hinges thus forming a door that is opened to replenish the supply of the individually wrapped tampons;
wherein a first rectangular aperture is provided at the bottom of the front wall to allow the individually wrapped tampons to exit from the enclosure;
wherein the pivoting compartment occupies the first rectangular aperture and prevents the individually wrapped tampons from falling out until one is needed;
wherein an axle for the pivoting compartment runs from the lower front corner of the left side wall to the lower front corner of the right side wall;
wherein a second rectangular aperture is provided at the lower rear of the left side wall or at the lower rear of the right side wall;
wherein the second rectangular aperture is provided to allow the drawer to slide out of the enclosure;
wherein the pivoting compartment is a container for the individually wrapped tampon that is about to be dispensed;
wherein the pivoting compartment is located at the bottom, front of the enclosure where it fills the first rectangular aperture in the front wall of the enclosure;
wherein the pivoting compartment comprises a hole that runs longitudinally through the pivoting compartment;
wherein the axle which is coupled to the left side wall of the enclosure and to the right side wall of the enclosure passes through the hole and allows the pivoting compartment to rotate;

wherein the pivoting compartment is cylindrical except that a flat face comprises a plane surface where the pivoting compartment would otherwise extend beyond the front wall of the enclosure, a concave trough comprises a curved and concave surface on the top of the pivoting compartment when the pivoting compartment is in a closed position, and a lip comprises a projection along the length of the pivoting compartment;

wherein when the pivoting compartment is in the closed position, the flat face aligns with the plane of the front wall for appearance purposes;

wherein the concave trough is provided to hold the individually wrapped tampon that will be dispensed next;

wherein the concave trough runs the entire length of the pivoting compartment;

wherein the concave trough extends from the upper edge of the flat face to the point where the angled slide meets the pivoting compartment;

wherein the depth of the concave trough allows the individually wrapped tampon to pass between the deepest part of the concave trough and the upper edge of the first rectangular aperture as the pivoting compartment rotates from the closed position to an open position;

wherein the lip extends radially away from the center of the pivoting compartment at the boundary between the flat face and the concave trough;

wherein the lip stops rotation of the pivoting compartment towards the closed position;

wherein the lip is adapted to provide an area where a user can grasp the pivoting compartment and move the pivoting compartment to the open position;

wherein the angled slide and the concave trough align in such a way that the individually wrapped tampons slide down the angled slide and into the concave trough without encountering an offset in height that would impede their movement;

wherein one or more springs cause the pivoting compartment to return to the closed position after each use;

wherein each of the one or more springs is a coil of wire with straight ends that extend beyond the diameter of the coil;

wherein one of the straight ends of the coil of wire presses against a first post and the other one of the straight ends presses against a second post;

wherein the first post is coupled to an interior surface of the a side wall of the enclosure;

wherein the second post is permanently coupled to the end of the pivoting compartment;

wherein the placement and orientation of the first post, the second post, and coil of wire is such that the coil of wire causes the pivoting compartment to rotate into the closed position;

wherein force applied to the lip to cause rotation of the pivoting compartment into the open position increases tension on the coil of wire such that when the lip is released the coil of wire causes the pivoting compartment to rotate back to the closed position.

2. The feminine hygiene product dispenser according to claim 1 wherein when the pivoting compartment is in the closed position, the individually wrapped tampon that is next to be dispensed drops into the concave trough located at the top of the pivoting compartment;

wherein if the pivoting compartment is rotated into the open position the individually wrapped tampon is moved out of the enclosure;

wherein when the lip is released, the pivoting compartment, now empty, returns to the closed position where the concave trough is refilled with another one of the individually wrapped tampons.

3. The feminine hygiene product dispenser according to claim 2 wherein the drawer comprises four side walls plus a drawer bottom;

wherein one of the four side walls is exposed outside of the enclosure and comprises a drawer pull;

wherein the drawer pull is accessible from outside of the enclosure and allows the drawer to be pulled open.

4. The feminine hygiene product dispenser according to claim 3 wherein the enclosure is wall-mounted using one or more mounting slots or the enclosure is free-standing by resting the bottom of the enclosure on a table, counter, or other horizontal surface.

5. The feminine hygiene product dispenser according to claim 4 wherein the enclosure is 6 inches +/−2 inches wide as measured from the left side wall to the right side wall, 6 inches +/−2 inches tall as measured from the top to the bottom, and 4 inches +/−1 inch deep as measured from the front wall to the rear wall.

* * * * *